(12) United States Patent
Gross

(10) Patent No.: US 7,632,297 B2
(45) Date of Patent: Dec. 15, 2009

(54) IMPLANT AND DELIVERY TOOL THEREFOR

(75) Inventor: Yosef Gross, Mazor (IL)

(73) Assignee: Prostaplant Ltd., Heerzilliya (IL)

( * ) Notice: Subject to any disclaimer, the term of this patent is extended or adjusted under 35 U.S.C. 154(b) by 779 days.

(21) Appl. No.: 11/325,731

(22) Filed: Jan. 5, 2006

(65) Prior Publication Data

US 2006/0173517 A1    Aug. 3, 2006

Related U.S. Application Data

(63) Continuation of application No. 10/736,740, filed on Dec. 17, 2003, now Pat. No. 7,004,965.

(51) Int. Cl.
  A61F 2/06 (2006.01)
  A61F 2/00 (2006.01)
(52) U.S. Cl. .............. 623/1.11; 623/1.15; 607/101
(58) Field of Classification Search .......... 623/1.11, 623/1.15, 1.42; 607/101, 102
  See application file for complete search history.

(56) References Cited

U.S. PATENT DOCUMENTS

| | | | |
|---|---|---|---|
| 5,160,341 A | 11/1992 | Brenneman et al. | |
| 5,776,142 A | 7/1998 | Gunderson | |
| 6,119,045 A | 9/2000 | Bolmsjo | |
| 6,231,516 B1 * | 5/2001 | Keilman et al. | 600/485 |
| 6,280,465 B1 | 8/2001 | Cryer | |
| 6,702,846 B2 | 3/2004 | Mikus et al. | |
| 6,709,452 B1 | 3/2004 | Valimaa et al. | |
| 6,991,647 B2 | 1/2006 | Jadhav | |
| 7,004,965 B2 | 2/2006 | Gross | |
| 7,104,949 B2 | 9/2006 | Anderson et al. | |
| 2002/0177904 A1 | 11/2002 | Huxel et al. | |
| 2004/0133263 A1 | 7/2004 | Dusbabek et al. | |
| 2004/0181287 A1 | 9/2004 | Gellman | |
| 2004/0254520 A1 | 12/2004 | Porteous et al. | |
| 2005/0216074 A1 | 9/2005 | Sahatjian et al. | |
| 2006/0276871 A1 | 12/2006 | Lamson et al. | |
| 2007/0106233 A1 | 5/2007 | Huang et al. | |

\* cited by examiner

*Primary Examiner*—Roy D Gibson
(74) *Attorney, Agent, or Firm*—Hoffman, Wasson & Gitler

(57) ABSTRACT

An implant system including a transurethral prostatic implant positioned in a prostate and including a lumen with an inner perimeter that surrounds an outer perimeter of a urethra at the prostate. The implant system may include a delivery tool including a shaft having a distal portion and an implant-holding portion proximal to the distal portion, the distal portion being sized for entry into a urethra, and the implant-holding portion being thicker than the distal portion, and an implant positioned on the implant-holding portion.

19 Claims, 4 Drawing Sheets

IMPLANT AND DELIVERY TOOL THEREFOR

This is a Continuation of application Ser. No. 10/736,740, filed Dec. 17, 2003 now U.S. Pat. No. 7,004,965.

FIELD OF THE INVENTION

The present invention relates generally to implants and delivery tools therefor, and particularly to an implant that is placed around a body lumen, such as but not limited to, a transurethral prostatic implant for treatment of benign prostatic hyperplasia (BPH).

BACKGROUND OF THE INVENTION

Benign prostatic hyperplasia (BPH) is a condition wherein a benign (non-cancerous) tumor with nodules enlarges the prostate gland. Although the growth is non-cancerous, as the tumor grows larger it can obstruct the urethra and interfere with the normal flow of urine.

Medications to treat BPH include alpha-1 blockers (doxazosin, prazosin, tamsulosin, and terazosin), which relax the muscles of the bladder neck, allowing easier urination. Finasteride is a drug that lowers prostate hormone levels, thus reducing the size of the prostate. Finasteride has been shown to increase urine flow rate and decrease the symptoms of BPH.

Surgery may be recommended for men with symptoms of incontinence, recurrent blood in the urine, urinary retention, and recurrent urinary tract infections. The choice of a specific surgical procedure is usually based on the severity of symptoms and the size and shape of the prostate gland.

Surgical treatment options include transurethral resection of the prostate (TURP), transurethral incision of the prostate (TUIP), and open prostatectomy. Other treatments include hyperthemia, laser therapy, and prostatic stents. Problems with stents are possible crustation, infection and epithelial irritation and inner growth.

Transurethral resection of the prostate (TURP) is the most common surgical treatment for BPH. TURP is performed by inserting a scope through the penis. The primary advantage of this procedure is that it does not involve an incision, thus reducing the risk of infection.

Other surgical approaches include the retropubic (behind the pubic structures) and suprapubic (above the pubic structures) open prostatectomies, which are done through an abdominal incision. The perineal surgical approach (through the region from the scrotum to the anus) is rarely used because the impotence rate after surgery may be as high as 50%.

Transurethral incision of the prostate (TUIP) is similar to TURP, but is usually performed in men who have a relatively small prostate. This procedure is usually performed on an outpatient basis and does not require a hospital stay.

The procedure is done through the penis without an incision. A small incision is made in the prostatic tissue to enlarge the lumen (opening) of the urethra and bladder outlet, thus improving the urine flow rate and reducing the symptoms of BPH. Eighty percent of the men who had this procedure reported some improvement in their symptoms. Possible complications include bleeding, infection, urethral stricture, and impotence.

An open prostatectomy is usually performed using general or spinal anesthesia. An incision is made through the abdomen or perineal area (i.e., through the pelvic floor, including the region from the scrotum to the anus). This is a lengthy procedure, and it usually requires a hospital stay of 5 to 10 days.

SUMMARY OF THE INVENTION

The present invention seeks to provide an innovative implant that is placed around a body lumen, as described more in detail hereinbelow. The implant of the invention is particularly useful in the treatment of BPH, and as such, a preferred embodiment is described hereinbelow that comprises a transurethral prostatic implant and delivery tool therefor. However, it is emphasized that the invention is not limited to a transurethral prostatic implant, and the invention may be used as an implant in other body lumens, such as but not limited to, blood vessels and lymph vessels.

There is thus provided in accordance with an embodiment of the present invention an implant system including a transurethral prostatic implant positioned in a prostate and including a lumen with an inner perimeter that surrounds an outer perimeter of a urethra at the prostate.

In accordance with an embodiment of the present invention the implant system includes a delivery tool including a shaft having a distal portion and an implant-holding portion proximal to the distal portion, the distal portion being sized for entry into a urethra, and the implant-holding portion being thicker than the distal portion, and an implant positioned on the implant-holding portion. (Again, the implant has a lumen with an inner perimeter greater in size than an outer perimeter of the urethra.)

Further in accordance with embodiments of the present invention, the implant may include a plurality of coils configured to corkscrew into tissue. The coils may or may not be continuous to one another. The coils may be coated with a substance. One or more of the coils may be energized to deliver RF energy or provide thermal energy. The implant-holding portion may be formed with screw threads corresponding to the pitch between the coils, and the implant may be initially positioned on the screw threads. A shoulder may be formed at a junction of the distal portion and the implant-holding portion. An implanting tool may be provided that includes a spiral pusher adapted for screwing onto the implant-holding portion of the shaft by rotation about a longitudinal axis of the shaft. Rotation of the implanting tool may cause the implant to unscrew off the implant-holding portion, advance distally off the shaft and corkscrew into tissue. The delivery tool may include a hollow lumen for passing therethrough at least one of a substance and a tool. The shaft may include a hollow lumen in fluid communication with a plurality of holes formed on a side wall of the shaft. A suction device may be in fluid communication with the holes that are on the side wall of the shaft.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENT

Figure 1:
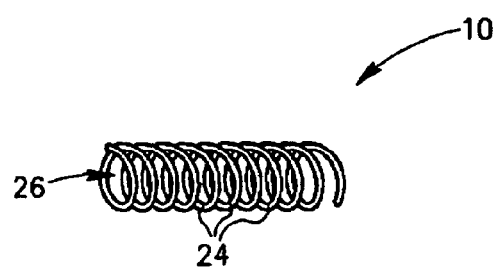
FIG. 1 is a simplified pictorial illustration of a transurethral prostatic implant, constructed and operative in accordance with an embodiment of the present invention.
Figure 2:
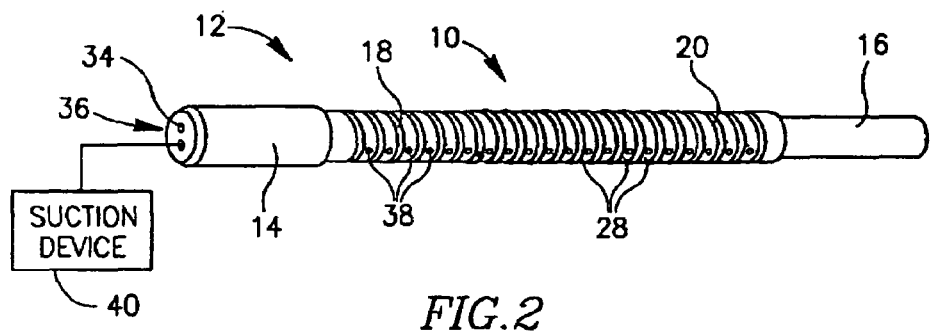
FIG. 2 is a simplified pictorial illustration of the transurethral prostatic implant of FIG. 1 mounted on a delivery tool, constructed and operative in accordance with an embodiment of the present invention.
Figure 3:
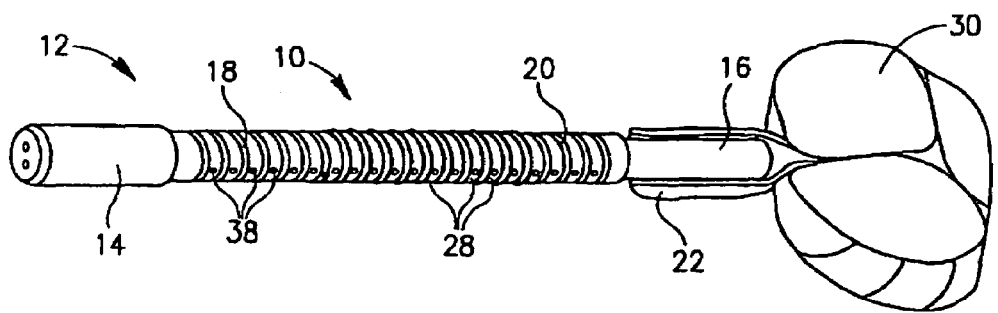
FIG. 3 is a simplified, partially cutaway illustration of the delivery tool of FIG. 2 being introduced into a urethra.

Reference is now made to FIGS. 1-3, which illustrate a transurethral prostatic implant 10 and delivery tool 12 therefor, constructed and operative in accordance with an embodiment of the present invention.

The delivery tool 12 may comprise a shaft 14 having a distal portion 16 and an implant-holding portion 18 proximal to the distal portion 16. A shoulder 20 may be formed at a junction of distal portion 16 and implant-holding portion 18. The distal portion 16 is sized for entry into a urethra 22 (FIG. 3). The implant-holding portion 18 is preferably thicker (e.g., larger in diameter) than the distal portion 16. The delivery tool 12 may be constructed of any suitable material, e.g., metal or plastic.

Transurethral prostatic implant 10 may be positioned on implant-holding portion 18. Implant 10 may be constructed of any suitable, medically-safe material, such as but not limited to, stainless steel, titanium, NITINOL and others. Implant 10 may comprise a plurality of coils 24 configured to corkscrew into tissue, as is described hereinbelow. For example, a distal, leading edge of the coils 24 may be sufficiently sharp to pierce tissue and corkscrew therein. The coils 24 may be continuous to one another, or alternatively, may be discrete coils. The coils 24 may be coated with a substance, such as but not limited to, a medication (e.g., beta blockers, antibiotics, etc.) or with an electrical insulator (e.g., TEFLON). One or more of the coils 24 (e.g., at the distal tip) may be energized to deliver RF energy, for example, to ablate tissue. Additionally or alternatively, one or more of the coils 24 (e.g., at the distal tip) may be energized to provide thermal energy (e.g., heating or cooling). The coils 24 may be of any shape or size, such as but not limited to, round, square, rectangular, etc.

Implant 10 has a lumen 26 with an inner perimeter greater in size than an outer perimeter of the urethra 22. The importance of this feature will become apparent hereinbelow.

The implant-holding portion 18 may be formed with screw threads 28 corresponding to the pitch (spacing) between coils 24. Accordingly, implant 10 may be initially positioned on screw threads 28.

Figure 7:
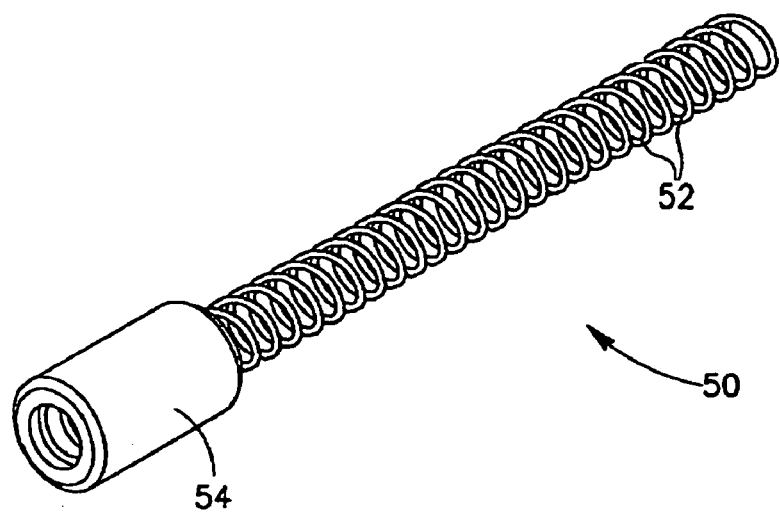
FIG. 7 is a simplified pictorial illustration of an implanting tool used to corkscrew the transurethral prostatic implant into tissue, constructed and operative in accordance with an embodiment of the present invention.
Figure 8:
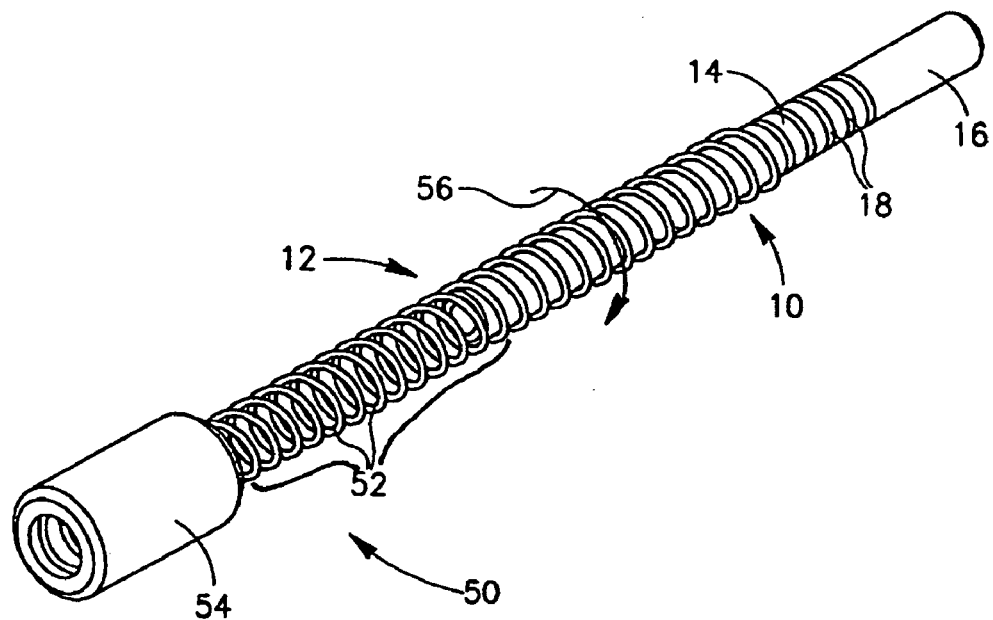
FIG. 8 is a simplified pictorial illustration of the implanting tool of FIG. 7 advancing the transurethral prostatic implant distally off the shaft of the delivery tool, in accordance with an embodiment of the present invention.

Reference is now made to FIGS. 7 and 8, which illustrate an implanting tool 50 used to advance transurethral prostatic implant 10 distally off the shaft 14 of the delivery tool 12, in accordance with an embodiment of the present invention. Implanting tool 50 may include a spiral pusher 52, constructed of a wire coil (e.g., stainless steel) with a pitch between coils corresponding to the pitch between coils 24. A proximal end of spiral pusher 52 may be mounted in a handle 54. As seen in FIG. 8, implanting tool 50 may be screwed onto the implant-holding portion 18 of shaft 14 by rotation about the longitudinal axis of shaft 14 in the direction of an arrow 56. As implanting tool 50 is rotated in the direction of arrow 56, it advances distally on shaft 14 and abuts against implant 10. Further rotation and distal advance of implanting tool 50 causes implant 10 to unscrew off implant-holding portion 18 and advance distally off shaft 14.

Reference is now made to FIGS. 3-6, which illustrate usage of the delivery tool 12. FIG. 3 illustrates the delivery tool 12 being introduced into the urethra 22.

Figure 4:
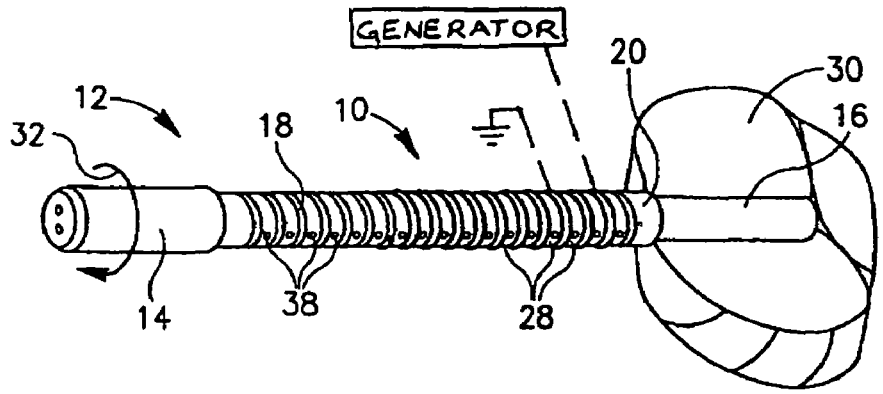
FIG. 4 is a simplified, partially cutaway illustration of the delivery tool of FIG. 2 after being introduced though the urethra up to a prostate.
Figure 5:
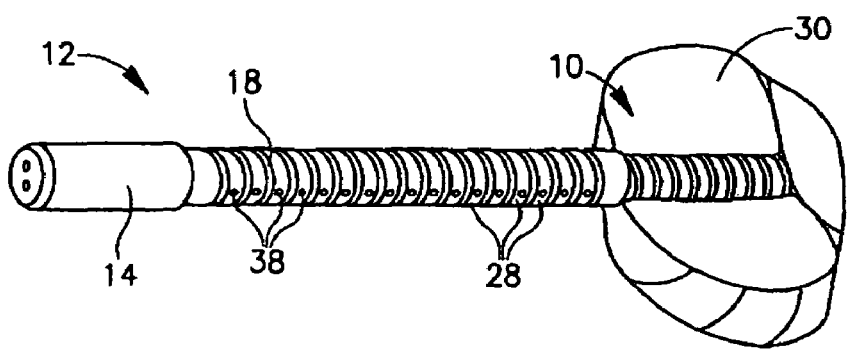
FIG. 5 is a simplified, partially cutaway illustration of the delivery tool of FIG. 2 introducing the transurethral prostatic implant into the urethra.
Figure 6:
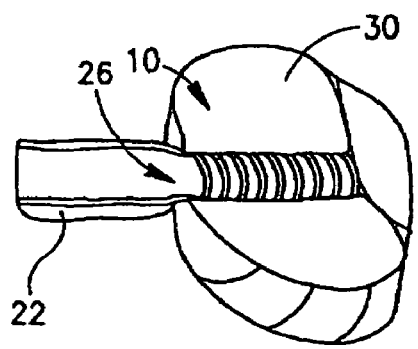
FIG. 6 is a simplified, partially cutaway illustration of the transurethral prostatic implant in place in the prostate and around the urethra, in accordance with an embodiment of the present invention.

FIG. 4 illustrates the delivery tool 12 having been introduced though the urethra 22 up to a prostate 30. At this point, shoulder 20 abuts against a surface of the prostate 30. Distal portion 16 opens the constricted urethra 22 to the desired diameter. As mentioned just before, suitable rotation and distal advance of implanting tool 50 (not shown in FIG. 4 for the sake of clarity) causes implant 10 to unscrew off implant-holding portion 18 and advance distally off shaft 14. As seen in FIG. 5, the implant 10 corkscrews into the prostate 30. Implant 10 is now positioned in the prostate 30 and the inner perimeter of lumen 26 surrounds the outer perimeter of the urethra 22 at the prostate 30. Thus, implant 10 supports the prostatic tissue surrounding the urethra 22 without touching the epithelium or other delicate tissue, and enlargens the area in the urethra 22 for urine to pass therethrough. Because the implant 10 does not contact the urethra 22, inflammation, crustation and disease may be reduced or prevented.

The delivery tool 12 may comprise a hollow lumen 34 for passing substances and/or tools therethrough, such as but not limited to, cooling fluid, medications, fiber optics, biopsy tools, optical devices (e.g., CCD) and/or imaging devices.

The shaft 14 may include a hollow lumen 36 in fluid communication with a plurality of holes 38 formed on a side wall of shaft 14 (such as but not limited to, distal portion 16). A suction device 40 may be in fluid communication with holes 38. By applying a vacuum (suction force) with suction device 40, the outer wall of the urethra 22 may be sucked into the hollow lumen 36 and help ensure that implant 10 surrounds and does not touch the outer wall of the urethra 22 when corkscrewing into the prostate 30.

Figure 9:
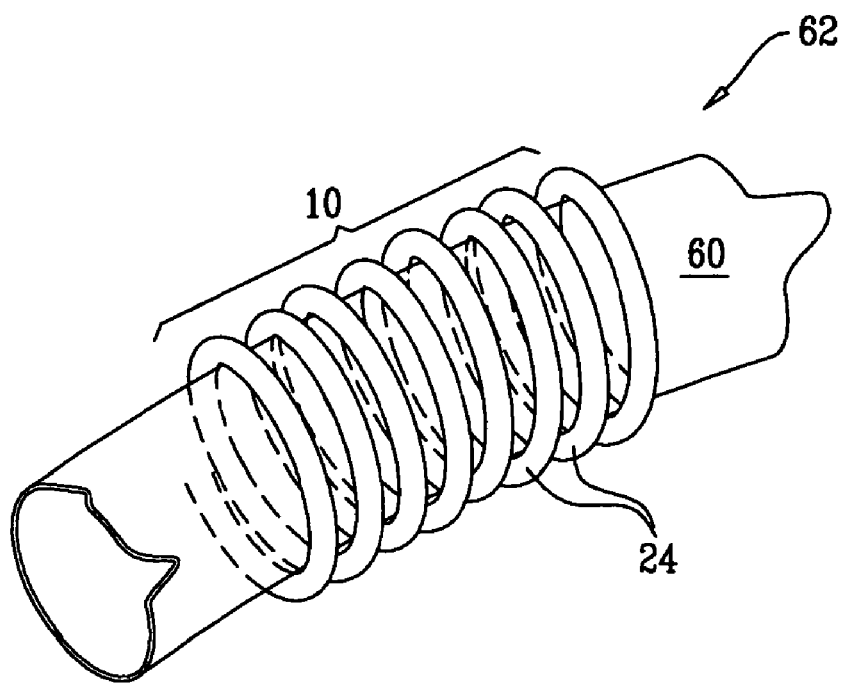
FIG. 9 is a simplified pictorial illustration of an implant, constructed and operative in accordance with an embodiment of the present invention, used to bolster a weakened blood vessel.

As mentioned above, the invention is not limited to the transurethral prostatic implant 10 described previously. Rather the invention may be used as an implant in other body lumens, such as but not limited to, blood vessels and lymph vessels. For example, as seen in FIG. 9, the implant 10 may be introduced to the site of an aneurysm (where there is a weakened wall 60 of a blood vessel 62), such as by means of a catheter or by as suitable surgical technique, wherein the coils 24 of implant 10 surround the wall 60 of the blood vessel 62. Implant 10 thus strengthens the weakened wall 60 and prevents further bulging outwards of the aneurysm. In such a case, the coils 24 may not necessarily corkscrew into some tissue, rather they envelope the aneurysm and bolster the blood vessel wall 60.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specifications and which are not in the prior art.

What is claimed is:

1. A method, comprising:
   distally advancing an implant including a plurality of coils through a body lumen of a patient; and
   supporting a wall of the body lumen by implanting the implant in tissue surrounding the body lumen.

2. The method according to claim 1, wherein supporting the wall of the body lumen comprises preventing outward bulging of the wall of the body lumen.

3. The method according to claim 1, wherein implanting the implant in the tissue surrounding the body lumen comprises implanting the implant in tissue surrounding a urethra of the patient.

4. The method according to claim 1, wherein implanting the implant in the tissue surrounding the body lumen comprises implanting the implant in tissue surrounding a blood vessel of the patient.

5. The method according to claim 1, wherein distally advancing the implant through the body lumen of the patient comprises rotating the implant about a longitudinal axis of a shaft used to implant the implant.

6. The method according to claim 1, further comprising imaging via apparatus used for distally advancing the implant.

7. The method according to claim 1, further comprising delivering thermal energy to the tissue surrounding the body lumen from one or more of the plurality of coils by energizing the one or more of the plurality of coils.

8. The method according to claim 1, further comprising delivering radiofrequency energy to the tissue surrounding the body lumen from one or more of the plurality of coils by energizing the one or more of the plurality of coils.

9. The method according to claim 1, wherein implanting the implant in the tissue surrounding the body lumen comprises corkscrewing the implant into the tissue surrounding the body lumen.

10. The method according to claim 9, wherein corkscrewing the implant into the tissue comprises rotating the implant about a longitudinal axis of a shaft used to implant the implant.

11. The method according to claim 9, wherein corkscrewing the implant into the tissue comprises surrounding an outer perimeter of the body lumen by an inner perimeter of the implant.

12. The method according to claim 11, wherein surrounding the outer perimeter of the body lumen comprises surrounding a urethra of the patient, and wherein corkscrewing the implant into the tissue comprises corkscrewing the implant into prostate tissue surrounding the urethra.

13. The method according to claim 11, wherein surrounding the outer perimeter of the body lumen by the inner perimeter of the implant comprises sucking the wall of the body lumen toward a center of the body lumen by applying a suction force in the body lumen.

14. A method, comprising:
   transurethrally advancing at least one prostatic implant through a urethra of a patient; and
   enlarging an area for urine to pass through the urethra, by supporting a prostate of the patient from outside the urethra, by piercing a site of the urethra and passing the prostatic implant through the site of the piercing into tissue of the prostate of the patient.

15. The method according to claim 14, wherein enlarging the area comprises supporting the tissue by the prostatic implant.

16. The method according to claim 14, wherein transurethrally advancing the at least one prostatic implant comprises transurethrally advancing a plurality of coils into the tissue of the prostate.

17. The method according to claim 14, wherein transurethrally advancing the at least one prostatic implant comprises transurethrally advancing a plurality of discrete implants.

18. Apparatus, comprising:
   a first transurethrally-deliverable coil-shaped implant; and
   a second transurethrally-deliverable coil-shaped implant, the second transurethrally-deliverable coil-shaped implant being discrete from the first transurethrally-deliverable coil-shaped implant, the first and second transurethrally-deliverable coil-shaped implants being implantable in tissue of a prostate of a patient from within a urethra of the patient, and configured to enlarge an area for urine to pass through the urethra by piercing a site of the urethra and supporting the prostate from outside the urethra.

19. The apparatus according to claim 18, wherein the first implant comprises a coil and wherein the second implant comprises a coil.

* * * * *